United States Patent
Fitzpatrick

(10) Patent No.: US 10,245,076 B2
(45) Date of Patent: Apr. 2, 2019

(54) METHOD OF INSTALLING A SPINAL IMPLANT ASSEMBLY

(71) Applicant: Fitzbionics Limited, Godalming, Surrey (GB)

(72) Inventor: Noel Fitzpatrick, Godalming (GB)

(73) Assignee: FITZBIONICS LIMITED (GB)

( * ) Notice: Subject to any disclaimer, the term of this patent is extended or adjusted under 35 U.S.C. 154(b) by 0 days.

(21) Appl. No.: 15/634,277

(22) Filed: Jun. 27, 2017

(65) Prior Publication Data

US 2017/0290609 A1 Oct. 12, 2017

Related U.S. Application Data

(63) Continuation of application No. 14/778,280, filed as application No. PCT/GB2014/050570 on Feb. 26, 2014, now abandoned.

(30) Foreign Application Priority Data

Mar. 18, 2013 (GB) .................................. 1304921.8

(51) Int. Cl.
*A61B 17/70* (2006.01)
*A61B 34/10* (2016.01)
(Continued)

(52) U.S. Cl.
CPC ...... *A61B 17/7037* (2013.01); *A61B 17/7002* (2013.01); *A61B 17/7005* (2013.01);
(Continued)

(58) Field of Classification Search
CPC .......................... A61B 17/7035–17/704; A61B 17/8605–17/862; A61B 17/864; A61B 17/8685; A61B 17/7055
See application file for complete search history.

(56) References Cited

U.S. PATENT DOCUMENTS

| 5,154,719 A | 10/1992 | Cotrel |
| 5,540,688 A | 7/1996 | Navas |

(Continued)

FOREIGN PATENT DOCUMENTS

| CN | 102579120 | 7/2012 |
| GB | 2479829 | 10/2011 |

(Continued)

OTHER PUBLICATIONS

UK Search Report, GB Patent Application 1304921.8, dated Dec. 2, 2013.
(Continued)

*Primary Examiner* — Eduardo C Robert
*Assistant Examiner* — Michelle C Eckman
(74) *Attorney, Agent, or Firm* — Andrus Intellectual Property Law, LLP

(57) ABSTRACT

A spinal implant assembly comprising an intervertebral device configured to be installed in a spinal disc space, the intervertebral device having a head component and a body component, the spinal implant assembly further comprising a coupling body for coupling the head component of the intervertebral device and an elongate member, the coupling body and head component each having a longitudinal axis, wherein the head component can be received by the coupling body with its longitudinal axis at a selected angle within a predetermined range of angles relative to the longitudinal axis of the coupling body.

17 Claims, 2 Drawing Sheets

(51) Int. Cl.
  *A61F 2/30* (2006.01)
  *A61F 2/44* (2006.01)
  *A61B 17/86* (2006.01)
  *A61B 17/00* (2006.01)

(52) U.S. Cl.
  CPC ...... *A61B 17/7032* (2013.01); *A61B 17/8685* (2013.01); *A61B 34/10* (2016.02); *A61F 2/30942* (2013.01); *A61F 2/446* (2013.01); *A61B 17/864* (2013.01); *A61B 2017/00526* (2013.01); *A61B 2034/108* (2016.02); *A61F 2002/30405* (2013.01); *A61F 2002/30434* (2013.01); *A61F 2002/30443* (2013.01); *A61F 2002/30622* (2013.01); *A61F 2002/449* (2013.01)

(56) References Cited

U.S. PATENT DOCUMENTS

| | | | |
|---|---|---|---|
| 5,591,166 A | | 1/1997 | Bernhardt |
| 5,658,285 A | * | 8/1997 | Marnay ............... A61B 17/7007 411/395 |
| 5,683,391 A | * | 11/1997 | Boyd ................ A61B 17/1637 606/264 |
| 5,752,957 A | * | 5/1998 | Ralph ............... A61B 17/7037 606/266 |
| 5,984,923 A | * | 11/1999 | Breard ............... A61B 17/7002 606/259 |
| 6,206,879 B1 | | 3/2001 | Marnay |
| 6,214,012 B1 | | 4/2001 | Karpman |
| RE37,161 E | | 5/2001 | Michelson |
| RE37,479 E | | 12/2001 | Kuslich |
| 6,325,827 B1 | * | 12/2001 | Lin ..................... A61B 17/025 623/17.16 |
| 6,428,575 B2 | * | 8/2002 | Koo ........................ A61F 2/446 623/17.11 |
| 6,432,140 B1 | | 8/2002 | Lin |
| 2001/0007941 A1 | * | 7/2001 | Steiner ............... A61B 17/7002 606/312 |
| 2002/0165613 A1 | | 11/2002 | Lin |
| 2002/0169507 A1 | | 11/2002 | Malone |
| 2008/0015596 A1 | * | 1/2008 | Whipple ............ A61B 17/7037 606/86 A |
| 2008/0046091 A1 | * | 2/2008 | Weiss .................. A61B 17/686 623/22.37 |
| 2008/0119857 A1 | | 5/2008 | Potash |
| 2010/0087861 A1 | * | 4/2010 | Lechmann ......... A61B 17/7002 606/257 |
| 2012/0253398 A1 | * | 10/2012 | Metcalf .............. A61B 17/7037 606/264 |
| 2013/0035724 A1 | * | 2/2013 | Fitzpatrick ........... A61B 17/686 606/272 |
| 2013/0245763 A1 | * | 9/2013 | Mauldin ................ A61F 2/4455 623/17.11 |
| 2016/0278815 A1 | * | 9/2016 | Fitzpatrick ......... A61B 17/7005 |
| 2017/0014162 A1 | * | 1/2017 | Fitzpatrick ......... A61B 17/7001 |
| 2017/0224393 A1 | * | 8/2017 | Lavigne ............. A61B 17/7098 |
| 2017/0231674 A1 | * | 8/2017 | Weiss ................. A61B 17/8095 606/301 |
| 2017/0245900 A1 | * | 8/2017 | Rezach ............. A61B 17/7055 |
| 2017/0290609 A1 | * | 10/2017 | Fitzpatrick ......... A61B 17/7037 |
| 2017/0354442 A1 | * | 12/2017 | Kim .................. A61B 17/7032 |

FOREIGN PATENT DOCUMENTS

| | | |
|---|---|---|
| WO | 199835636 | 8/1998 |
| WO | 2008024373 | 2/2008 |

OTHER PUBLICATIONS

International Search Report, PCT/GB2014/050570, dated May 8, 2014.

* cited by examiner

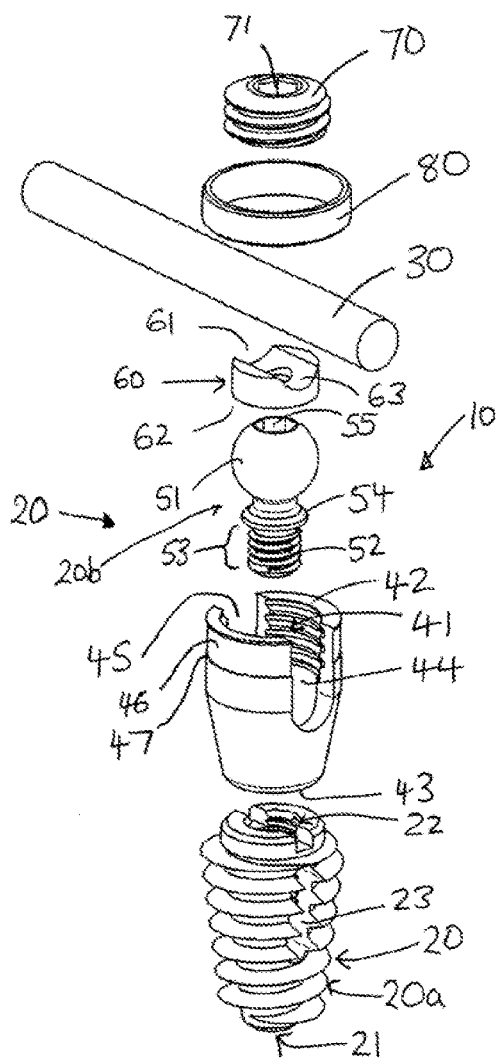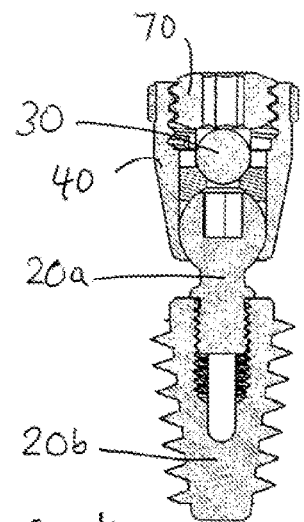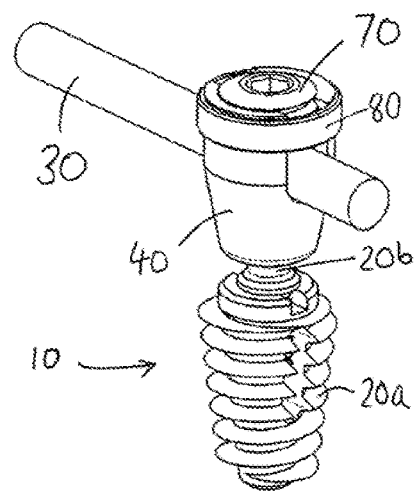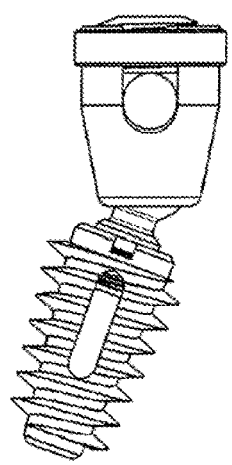

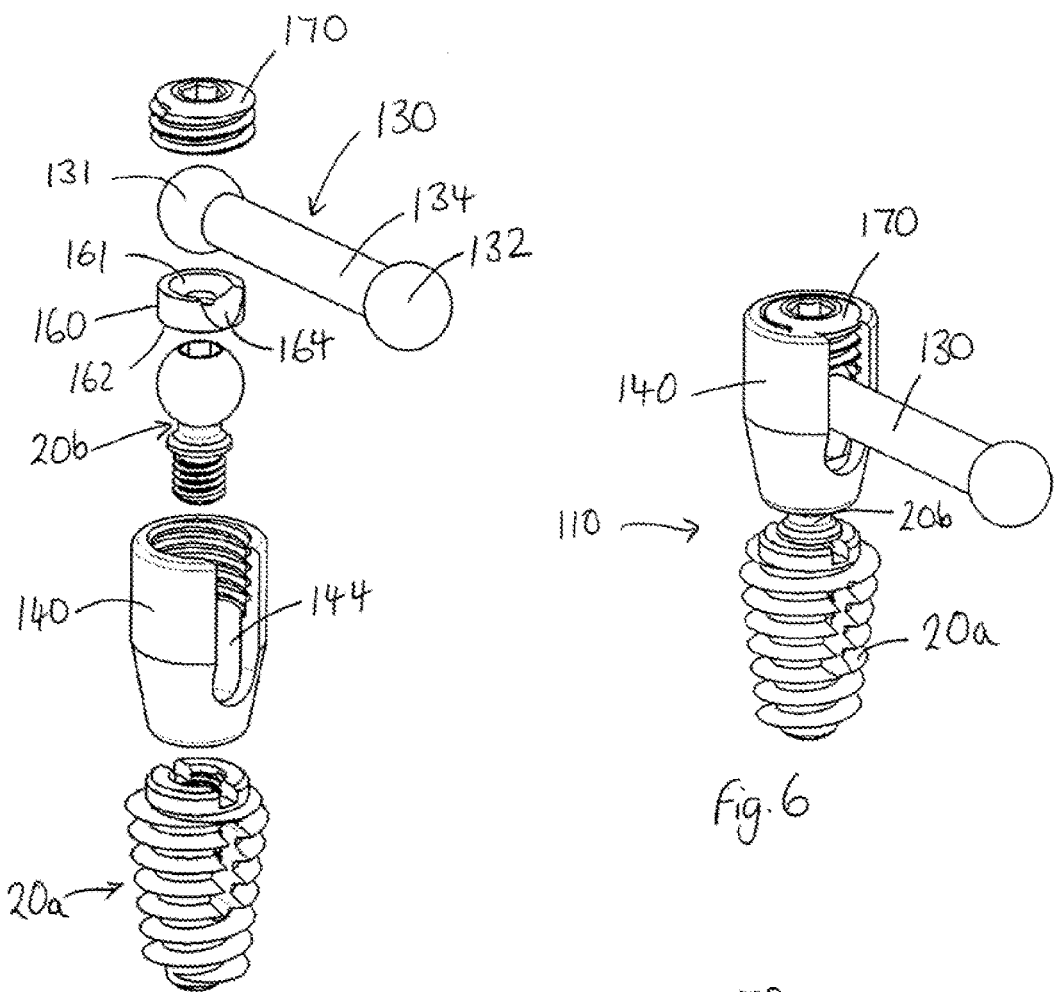
Fig. 5
Fig. 6
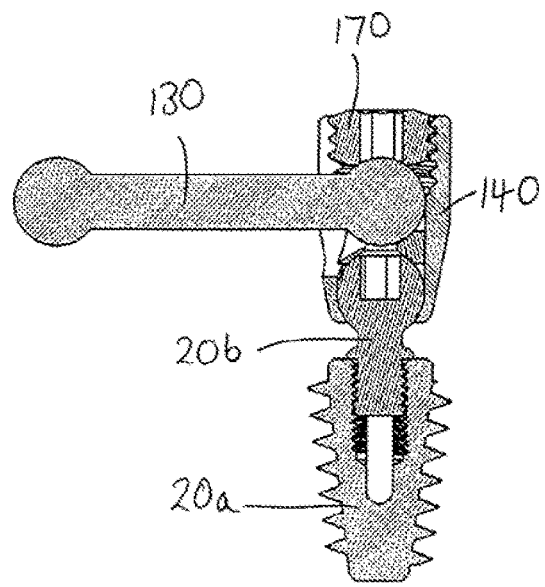
Fig. 7

METHOD OF INSTALLING A SPINAL IMPLANT ASSEMBLY

CROSS REFERENCE TO RELATED APPLICATION

This application is a continuation of U.S. patent application Ser. No. 14/778,280 filed Sep. 18, 2015.

FIELD OF THE INVENTION

The invention relates to a spinal implant assembly. More specifically the invention relates to assemblies with parts for implantation into intervertebral space between adjacent vertebrae of the spine.

BACKGROUND TO THE INVENTION

The spine or vertebral column comprises a plurality of separate vertebrae. The vertebrae are movable relative to one another, and separated from one another by fibrocartilage called inter-vertebral discs.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. The intervertebral discs provide mechanical cushion between adjacent vertebrae. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve immobilization by implanting artificial assemblies in or on the spinal column.

In order to treat certain injuries or conditions of the spinal column an intervertebral device may be placed in the intervertebral disc space to fuse or promote fusion of adjacent vertebrae. Such fusion devices are often used in combination with stabilisation systems wherein a metal rod that is bendable to match the natural curvature of the spine is mechanically attached at strategically selected vertebrae, allowing the rod to be rigidly fixed to the spine. This provides a rigid support to the spinal column. For this, pedicle screws located in the bone structure are typically fixed to a specially designed clamp to attach to a spinal rod. A problem with these stabilisation systems is that parts of the vertebra cannot stably receive a bone screw, or can only receive a bone screw screwed in at a certain angle. Also, for spinal fixings for small animals, within the confined spaces allowed therein, conventional rod anchoring methods are not suitable since the placement of the pedicle screw and the direction of the rod cannot be matched adequately. A system that can be used in small animals is needed, wherein confined spaces make conventional rod anchoring systems unsuitable. Furthermore, many devices for providing positioning of bone screws with respect to a stabilising rod loosen over time, providing an unstable joint. There is therefore a need for a solution that overcomes one or more of these problems.

SUMMARY OF INVENTION

According to a first aspect of the invention there is provided a spinal implant assembly comprising an intervertebral device configured to be installed in a spinal disc space, the intervertebral device having a head component and a body component, the spinal implant assembly further comprising a coupling body for coupling the head component of the intervertebral device and an elongate member, the coupling body and head component each having a longitudinal axis, wherein the head component can be received by the coupling body with the longitudinal axis of the head component at a selected angle within a predetermined range of angles relative to the longitudinal axis of the coupling body. Suitably the head component can be adjusted polyaxially relative to the coupling body.

The intervertebral device provides a stable anchorage for the spinal stabilisation system provided by the elongate member.

Suitably the spinal implant assembly can be adapted to provide a locked configuration, wherein the head component and/or elongate member are locked in position relative to the coupling body, and an adjustable configuration, wherein the position of the head component and/or elongate member relative to the coupling body can be adjusted.

Preferably the assembly further comprises an elongate member, the coupling body receiving the elongate member and the head component of the intervertebral device when assembled.

The head component and body component can be integral, however preferably are releasably attachable to one another.

Preferably the head component of the intervertebral device is releasably attachable to the body component via a threaded connection.

Preferably the head component has a head portion and a shank portion, the shank portion being at least partially externally threaded, the body component having a bore with a first open end, the bore being at least partially internally threaded, the internal threads of the bore corresponding with the external threads of the shank portion of the head component such that the head component is releasably attachable to the body component.

Preferably the head portion of the head component is at least partially spherical.

Preferably the coupling body comprises a hollow tubular body, the head portion of the head component being receivable in the hollow tubular body.

Preferably the coupling body has a first opening in a first end and a second opening in a second end, the first opening being larger in diameter than that of the head portion and the second opening being smaller in diameter than that of the head portion, a portion of the inner surface of the coupling body having a concavely curved inner surface, the curved inner surface corresponding with the at least partially spherical head portion, such that the head component may be positioned polyaxially relative to the coupling body when assembled.

Preferably the coupling body has at least a first slot. Suitably the elongate member suitably extends through the first slot when assembled with the coupling body. The slot communicates with the first open end of the coupling body. In some embodiments, when assembled, the elongate member can pivot relative to the coupling body, within the first slot, over a pre-determined range of motion.

Preferably the coupling body has a second slot. Suitably the elongate member extends through the second slot when assembled with the coupling body. The first and/or second slots preferably are elongate, the or each slot having a longitudinal axis parallel with the longitudinal axis of a bore of the coupling body. Where the elongate member is a rod, the elongate member will extend through both the first and second slots when assembled, the first and second slots effectively providing a rod receiving channel.

Preferably the elongate member comprises a rod.

Preferably the elongate member has a first end that is at least partially spherical. Preferably the elongate member has a second end that is at least partially spherical.

Preferably the assembly further comprises a washer for location between the head component and the elongate member when assembled.

Preferably the washer has first and second opposing surfaces, the first surface being concavely curved and facing the first end of the elongate member when assembled. Such a washer will be used to engage the elongate member when it has a first end that is at least partially spherical.

Preferably the washer has first and second opposing surfaces, the first surface having an elongate groove for receiving the elongate member when assembled. Such embodiments are suitable for use with a rod-like elongate member.

Preferably the washer has first and second opposing surfaces, the second surface being concavely curved and facing the head component when assembled.

Preferably at least part of the body component of the intervertebral device is externally tapered.

Preferably the body component has a proximal end and a distal end and the external taper of the body component tapers towards the proximal end of the bolt. In this context the term proximal used in relation to parts of spinal implants or spinal fixings means located nearer or towards the centre of the subject's body or spine when the implant part or fixing part is installed and distal means located away from the centre of the body or spine when the implant part or fixing part is installed. The term subject as used herein can be a human or animal subject.

The maximum diameter of the body component at any point along its longitudinal axis is greater than the opening in the second open end of the coupling body. In this way, the coupling body can be compact whilst the body component can be large in diameter, suitable for vertebral distraction and stable anchoring in the disc space.

Preferably at least part of the body component is externally threaded.

Preferably the body component has a hollow bore.

Preferably the head component has a shank portion insertable within the hollow bore of the body component, the shank portion of the head component being shorter in length than the hollow bore of the body component such that with the shank portion fully inserted in the body component, at least some hollow space in the hollow bore remains unoccupied by the shank portion. This allows for bone ingrowth into the body component when installed, thus improving the stability of the anchorage.

Preferably the body component has at least one aperture, the aperture communicating with the hollow bore. Suitably said at least one aperture is not obscured, or is only partially obscured, by the shank portion of the head component when assembled, such that the aperture communicates with the hollow bore when the spinal implant assembly is assembled.

Preferably at least part of the body component is hydroxyapatite coated.

Preferably the assembly further comprises a compression member for compressing the elongate member and the head component in locking engagement within the coupling body.

Preferably the compression member is a locking screw. The locking screw may be externally threaded, the coupling body having a bore with first and second open ends, at least part of the bore being internally threaded, the internal threads of the bore corresponding with the external threads of the locking screw. Preferably the assembly further comprises a ring, configured to be received around the coupling body when assembled.

There is also provided a spinal implant system comprising two or more spinal implant assemblies according to any previous aspect of the invention and an elongate member, wherein the assemblies are configured to be coupled together using the elongate member. This provides a system wherein a first implant assembly can be installed in a first disc space and a second implant assembly can be installed in a second, adjacent disc space, and the spine can be stabilised by the coupling of the implant assemblies using the elongate member. Further implant assemblies installed in further disc spaces can be assembled, all being coupled by a single elongate member. Alternatively a first implant assembly can be installed in a disc space and a second implant assembly can be installed in the same disc space.

The assembly can also be used as part of a spinal implant system comprising a spinal implant assembly according to any preceding claim and an elongate member, wherein the system further comprises a spinal fixing comprising a bone fastener configured to be installed into bone and a coupling body for receiving the bone fastener and said elongate member such that the elongate member couples the spinal implant assembly and spinal fixing when the system is assembled. The bone fastener may be a pedicle screw for example, suitable for installation into a vertebra.

There is also provided a kit for assembly into a spinal implant assembly or system, wherein the kit comprises the parts of the assembly according to any previous aspect of the invention. A modular kit can be provided wherein intervertebral devices of differing dimensions are provided, for example.

There is also provided a computer program embodied on a computer readable medium for manufacturing a spinal implant assembly or system to any previous aspect of the invention.

There is also provided a method of installing a spinal implant assembly, the method comprising the steps of providing a spinal implant assembly, the spinal implant assembly comprising an intervertebral device configured to be installed in a spinal disc space, the intervertebral device having a head component and a body component, the spinal implant assembly further comprising a coupling body for coupling the head component of the intervertebral device and an elongate member, the coupling body and head component each having a longitudinal axis, wherein the head component can be received by the coupling body with its longitudinal axis at a selected angle within a predetermined range of angles relative to the longitudinal axis of the coupling body, the method further comprising implanting the body component of the intervertebral device between adjacent vertebrae or between a vertebra and the sacrum;

coupling the intervertebral device with the coupling body, before or after implanting the body component, wherein the head component can be received by the coupling body such that its longitudinal axis is at a selected angle within a predetermined range of angles relative to the longitudinal axis of the coupling body.

BRIEF DESCRIPTION OF THE DRAWINGS

A preferred embodiment of the present invention will now be more particularly described by way of example only with reference to the accompanying drawings, wherein:

FIG. 1 is an exploded view of a spinal implant assembly;

FIG. 2 is a perspective view of the assembly of FIG. 1, assembled together;

FIG. 3 is a side view of the assembly of FIG. 2, but with the longitudinal axis of the intervertebral device shown non-parallel with that of the coupling body;

FIG. 4 is a cross-sectional view of the assembly of FIG. 2;

FIGS. 5 to 7 show another embodiment, similar to that of FIGS. 1 to 4, but wherein the elongate member is a dumbbell rather than a rod;

FIG. 5 is an exploded view of a spinal implant assembly;

FIG. 6 is a perspective view of the assembly of FIG. 4, assembled together;

FIG. 7 is a cross-sectional view of the assembly of FIG. 6.

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Referring to FIG. 1, this shows a spinal implant assembly 10 according to a first embodiment. The assembly can be used to fuse two or more vertebra together, in order and to provide stabilisation of the spine. The assembly 10 comprises an intervertebral device 20, an elongate member 30 and a coupling body 40. The assembly is designed such that the intervertebral device 20 can be coupled for multiaxial positioning relative to the coupling body 40 and elongate rod 30.

The intervertebral device 20 comprises a body component 20a and a head component 20b. The body component 20a of the intervertebral device is configured for installation in a spinal disc space between any two vertebrae of a subject, including the space between the sacrum and the adjacent vertebra. The body component 20a of the intervertebral device is a tapered bolt that can be used to induce fusion and distraction when implanted. The bolt 20a has a proximal end 21 and a distal end 22, and is tapered towards the proximal end 21. The external surface of the bolt 20a is threaded with deep threads for cutting into vertebral bone on either side of the spinal disc space. The threads are thin in section and very pronounced, to cut into the bone and aid the insertion process.

The bolt 20a has a hollow bore. The proximal end 21 is closed and the distal 22 end is open. Alternatively, the proximal end 21 may be open. The hollow bore is internally threaded, at least partially, at or near the distal end 22 of the bolt.

The bolt has a first elongate slot 23, having a longitudinal axis running parallel with the longitudinal axis of the bolt 20. The bolt has a second elongate slot opposite the first elongate slot (not visible in the figures). The bolt may have more than two elongate slots. The outer surface of the bolt 20 may have a hydroxyapatite coating to stimulate bone ingrowth.

The head component 20b of the intervertebral device has a head portion 51 and a shank portion 52. The shank portion 52 has an externally threaded portion 53 and an enlarged shoulder 54. The externally threaded shank portion 52 is receivable within the hollow bore of the bolt 20a, the external threads of the shank portion 52 corresponding with the internal threads of the hollow bore of the bolt 20a, such that the head component 20b is releasably attachable to the bolt 20a. The enlarged shoulder 54 butts up against the distal end 22 of the bolt 20a when the shank portion 52 is fully inserted in the bolt 20a.

The head portion 51 and shank portion 52 of the head component 20b are preferably integral with one another. The head portion 51 comprises a substantially spherical head with a female recess 55 at its distal end. The recess is hexagonal in shape. The recess 55 can receive a wrench or other torque-transferring tool, for transferring torque to the head component 20b during assembly, to assemble it to the bolt 20a. Alternatively, the recess 55 may be a shape other than hexagonal, the shape being suitable for receiving torque transfer from a suitable tool. In an alternative embodiment the head portion 51 can comprise a part-spherical portion and removable rocker, to form a substantially complete ball end. The term part-spherical as used herein refers to a surface that comprises a portion of a sphere.

The coupling body 40 comprises a tubular, hollow body. The coupling body 40 has a bore 41 having first and second open ends. The first and second open ends each have an opening that is circular in shape 42,43, the first opening communicating with first and second elongate slots 44, 45, disposed in opposite sides of the coupling body 40. The elongate slots 44,45 extend from the first opening 42, part of the way down the side of the coupling body 40. The elongate slots 44, 45 form a channel for receiving the elongate member 30 when assembled. The second opening 43, in the proximal end, is smaller in diameter than the first opening 42. The first opening 42 is large enough to receive the head portion 51 of the head component 20b therethrough. The second opening 43 is surrounded by a curved inner surface, internally to the coupling body 40. The curvature of the curved inner surface corresponds to the curvature of the head portion 51, such that the head portion 51 can pivot smoothly in the coupling body 40 within a pre-determined range of angles relative to the coupling body 40 when the head component 20b is received within the coupling body 40.

The assembly further comprises a washer 60, located between the head component 20b and the elongate member 30 when assembled. The washer 60 is circular in shape, having first and second opposing surfaces 61, 62 (top and bottom surfaces, or distal and proximal surfaces). The first surface 61 has an elongate groove 63 for receiving the elongate member 30 when assembled. The second surface 62 is concavely curved (not visible in the figures). The groove 63 in the first surface and concavely curved second surface form sockets for receiving the elongate member 30 and head portion 51 respectively. The intermediate conforming washer 60 increases the surface contact area that would exist between the head portion 51 and the elongate member 30, if the washer were not present. The washer allows the distribution of loads evenly between the head portion 51 and the elongate member 30.

In some embodiments the sockets in the washer conform in shape with the corresponding piece of the assembly to be received therein. In alternative embodiments, the first and second surfaces of the washer may include one or more points or edges that, when the assembly is subjected to compressive force by a locking member 70 (described below), bite into the respective members the washer engages with. The axial mouth of the groove 63 may have a transverse diameter that is smaller than the radius of the elongate member. Similarly the radius of curvature of the second surface 62 may be slightly less than the radius of curvature of the head portion 51. This non-conformance between the sockets in the first and second surfaces of the washer and the corresponding head portion and elongate member provides an edge contact between the socket and the member to be received therein, which enhances the locking mechanism provided by the washer.

The elongate extension 30 is a rod. The rod may of course be long or short, and may be fixed to the subject using another fixing device at its end or at one or more points along the length of the rod. The rod may be longer than as shown in FIGS. 1 to 3. The rod may be straight or curved. The rod may be flexible, such that it can be curved into a desired shape by the surgeon during installation.

The assembly further comprises a locking screw 70, which acts as a compression member in use, to compress the elongate member 30, washer 60, and head component 20*b* together, against the inside of the coupling body 40, and therefore to lock the head component 20*b* at a selected angular orientation relative to the coupling body 40. The locking screw 70 has a circular cross-section, and has externally threaded sides. The coupling body 40 has internal threading on at least part of its internal surface, near to the first opening 42. The internal threads of the coupling body 40 correspond with the external threads of the locking screw 70. The locking screw 70 can be screwed into the first opening 42 of the coupling body, thus providing a compressive force on the elongate member 30, washer 60 and head component 20*b*. The locking screw 70 has a hexagonal shaped recess 71 in its top surface (distal surface), which can receive a hexagonal shaped torque-transferring tool for tightening the locking screw 70 in threaded engagement in bore 41. Alternatively the recess 71 may be a shape other than hexagonal, the shape being suitable for receiving torque transfer from a suitable tool.

The FIG. 1 embodiment also includes a further optional feature, ring 80. The ring 80 is a circular piece which is shaped and dimensioned to sit in a recessed region 46 in the outer wall of the distal end of the coupling body 40, as shown assembled in FIG. 2. The ring 80 is placed in the recessed region 46, the ring 80 butting up against a shoulder on the outer wall of the coupling body 40. The ring 80 is usually placed around the coupling body 40 before the locking screw 70 is tightened. The ring 80 captivates the distal end of the coupling body 40, preventing the split distal end of the coupling body from springing apart as the locking screw 70 is tightened. The ring is shown in the embodiment of FIGS. 1 to 4, but it is an optional part of the assembly.

In operation, in order to assemble the spinal implant assembly and install it in a subject, the shank portion 52 of the head component 20*b* is inserted, through the first opening 42, then through the second opening 43 of the bore 41 of the coupling body 40, until the head portion 51 butts up against the internal edges of the second opening 43. A torque-transferring tool, such as a wrench, is received in recess 55 to threadedly secure the head component 20*b* to the bolt 20*a*. The bolt 20*a* may already be installed in a subject's disc space or may be installed in a subject's disc space after the head component 20*b* with coupling body 40 assembled thereto is secured to the bolt 20*a*.

When installing the bolt 20*a* in the subject it is inserted in the disc space between adjacent vertebrae or at the lumbosacral joint. The threads on the external surface of the bolt 20*a* cut into the bone during insertion. The hollow bore of the bolt 20*a* can be impregnated with bone graft before insertion of the bolt 20*a* in the subject. The subject's bone will ingrow, through the elongate slots 23, and attach with the bone graft inside the hollow section of the bolt 20*a*. This further anchors the bolt 20*a* in the subject. Even if no bone graft is inserted in the hollow of the bolt 20*a* before implantation of the bolt 20*a* into the subject, cutting of the subject's bone by the bolt threads as the bolt is inserted will create bone debris that will accumulate, via the elongate slots 23, in the hollow bore of the bolt 20*a*. The subject's bone will ingrow, through the elongate slots 23, and attach with the accumulated bone debris, further anchoring the bolt 20*a* against rotation.

The washer is then inserted in the coupling body, with the second surface 62 facing the head component 20*b*, then the elongate member 30 is inserted in the slots 44, 45 of the coupling body 40.

With the assembly assembled as described above, the coupling body 40 can pivot relative to the anchored intervertebral device 20 (comprising the bolt 20*a* and head component 20*b*), giving rise to polyaxial positioning within a predetermined angle range. Therefore, the assembly is in this adjustable configuration, it provides a polyaxial or universal joint between the bolt 20*a* and the coupling body 40 and also between the bolt 20*a* and the elongate member 30. The elongate extension can slide within the slots 44, 45, relative to the coupling body 40. The locking screw 70 can be tightened within the threaded bore 41, with the ring 80 in place around the coupling body 40, to compress the head component 20*b*, washer 60 and elongate member 30 together, against the inside of the coupling body 40, until the elongate member 30 and intervertebral device 20 are locked, relative to the coupling body, such that they can no longer be positionally adjusted. An assembled device is shown in FIG. 2. A further assembled device in which the longitudinal axis of the intervertebral device 20 is non-parallel with that of the coupling body 40 is shown in FIG. 3.

The spinal implant assembly can be provided as part of a system in which two or more spinal implant assemblies, as described above, are coupled by a single elongate member 30. A first implant assembly can be installed in a first disc space and a second implant assembly can be installed in a second, adjacent disc space, and the spine can be stabilised by the coupling of the implant assemblies using the elongate member. Alternatively a first implant assembly can be installed in a disc space and a second implant assembly can be installed in the same disc space.

Instead of a bolt, the body component 20*a* may be an interbody cage.

The spinal implant assembly can also be provided as part of a system in which one or more spinal implant assemblies, as described above, are coupled to at least one spinal fixing having a simple pedicle screw or other bone fixing means, which is coupleable to the elongate member 30 via a suitable coupling body.

FIGS. 5 to 7 show an alternative embodiment for a spinal implant assembly 110 similar to that of FIGS. 1 to 4. The same reference numerals have been used in FIGS. 5 to 7 to refer to components which are substantially the same as those in the previous embodiment. The implant assembly 110 differs from that of FIGS. 1 to 4 in that the elongate member 130 in the FIG. 5 embodiment has first and second ball ends 131, 132 joined by a rod portion 134. Each ball end 131, 132 is substantially spherical, such that the elongate member 130 is like a dumbbell. Each ball end 131, 132 can have a diameter that is substantially the same as that of the head portion 51 of head component 20*b*.

For the embodiment of FIG. 5, both the first and second surfaces 161 of the washer 160 will be concavely curved. The washer 161 has a notch 164 extending between the first surface 161 and the side of the washer. When assembled, the notch 164 faces toward the rod portion 134 of the elongate member 130.

The coupling body 141 only has one slot 144 (although it can have a second slot on the opposing side).

The underside 171 of the locking screw 170 has a concavely curved surface corresponding with the curvature of the first ball end 131 of the elongate member 130. The elongate member can pivot relative to the coupling body 140, along the axis of slot 144, when the locking screw 170 is not fully tightened. The notch 164 in the washer 160 allows for a greater range of movement when the elongate member 130 pivots within slot 144.

The second ball end 132 can be received within the coupling body 40 of a second spinal implant assembly like that of FIG. 5, or some other spinal implant assembly (such as an assembly including a pedicle screw rather than an intervertebral device with detachable head component).

In alternative embodiments, the elongate member 130 may have only a first ball end 130 which is received by the coupling body 40, the elongate member forming a simple rod extending from the first ball end 130.

Like the embodiment of FIGS. 1 to 4, the assembly of FIGS. 5 to 7 allows polyaxial positioning of the bolt 20a relative to the coupling body 140 when the assembly is in an adjustable configuration (when the locking member 170 is not tightly compressing the assembly components) but not when the assembly is in a locked configuration (when the locking member not tightly compressing the assembly components).

The embodiment of FIGS. 5 to 7 is installed in a very similar manner to that of FIGS. 1 to 4.

The invention claimed is:

1. A method of installing a spinal implant assembly in a first disc space in a subject's spine, the method comprising the steps of
providing a first spinal implant assembly, the first spinal implant assembly comprising an intervertebral device configured to be installed in a spinal disc space, the intervertebral device having a head component and a body component, the first spinal implant assembly further comprising a coupling body for coupling the head component of the intervertebral device with an elongate member, the coupling body and head component each having a longitudinal axis, wherein the head component can be received by the coupling body with the longitudinal axis of the head component at a selected angle within a predetermined range of angles relative to the longitudinal axis of the coupling body, wherein at least part of the body component of the intervertebral device is externally tapered and at least part of the body component is externally threaded;
implanting the body component of the intervertebral device into a first disc space between a pair of adjacent vertebrae or between a vertebra and the sacrum so as to cause distraction of the disc space or at the lumbosacral joint;
coupling the intervertebral device with the coupling body, before or after implanting the body component, such that the longitudinal axis of the intervertebral device is at a selected angle within a predetermined range of angles relative to the longitudinal axis of the coupling body;
wherein the head component has a head portion and a shank portion, the shank portion being at least partially externally threaded, the body component having a bore with a first open end, the bore being at least partially internally threaded, the internal threads of the bore corresponding with the external threads of the shank portion of the head component such that the head component is releasably attachable to the body component,
wherein the head portion of the head component is at least partially spherical, the coupling body comprising a hollow tubular body and having a proximal end and a distal end, the head portion of the head component being receivable in the hollow tubular body and wherein the coupling body has a first opening in the distal end of the coupling body and a second opening in the proximal end, the first opening being larger in diameter than that of the head portion and the second opening being smaller in diameter than that of the head portion, the first opening being large enough to receive the head portion of the head component therethrough, and the second opening being sized such that the shank portion of the head component may pass through, a portion of the inner surface of the coupling body having a concavely curved inner surface, the curved inner surface corresponding with the at least partially spherical head portion, such that the head component butts up against the curved inner surface and may be positioned polyaxially relative to the coupling body when assembled.

2. A method according to claim 1, wherein the method further comprises providing an elongate member, the coupling body being configured to receive the elongate member and the head component of the intervertebral device when assembled, the method further comprising coupling the elongate member to the coupling body.

3. A method according to claim 2, the method further comprising
providing a second spinal implant assembly for installing in a second disc space, adjacent the first disc space, the second spinal implant assembly comprising an intervertebral device configured to be installed in a spinal disc space, the intervertebral device having a head component and a body component, the second spinal implant assembly further comprising a coupling body for coupling the head component of the intervertebral device and the elongate member, the coupling body and head component each having a longitudinal axis, wherein the head component can be received by the coupling body with the longitudinal axis of the head component at a selected angle within a predetermined range of angles relative to the longitudinal axis of the coupling body, wherein at least part of the body component of the intervertebral device is externally tapered and at least part of the body component is externally threaded;
implanting the body component of the second spinal implant assembly into the second disc space, between the corresponding adjacent vertebrae, so as to cause distraction of the second disc space;
coupling the intervertebral device of the second spinal implant assembly with its corresponding coupling body, before or after implanting the body component, such that the longitudinal axis of the intervertebral device is at a selected angle within a predetermined range of angles relative to the longitudinal axis of the coupling body;
and coupling the elongate member with the coupling body of the second spinal implant assembly so as to couple the first and second spinal implant assemblies together using the coupling body.

4. A method according to claim 1, wherein the method further comprises releasably attaching the head component of the intervertebral device to the body component.

5. A method according to claim 1, wherein the method further comprises releasably attaching the head component of the intervertebral device to the body component via a threaded connection.

6. A method according to claim 1, wherein the coupling body has at least a first slot.

7. A method according to claim 6, wherein the coupling body has a second slot.

8. A method according to claim 1, wherein the elongate member comprises a rod.

9. A method according to claim 1, wherein the elongate member has a first end that is at least partially spherical.

10. A method according to claim 9, wherein the elongate member has a second end that is at least partially spherical.

11. A method according to claim 1, wherein the spinal implant assembly further comprises a washer for location between the head component and the elongate member when assembled, the method further comprising locating the washer between the head component and the elongate member.

12. A method according to claim 11, wherein the washer has first and second opposing surfaces, the first surface being concavely curved and facing the first end of the elongate member when assembled.

13. A method according to claim 12, wherein the washer has first and second opposing surfaces, the first surface having an elongate groove for receiving the elongate member when assembled.

14. A method according to claim 1, wherein the body component has a proximal end and a distal end and the external taper of the body component tapers towards the proximal end of the bolt.

15. A method according to claim 1, wherein the body component has a hollow bore.

16. A method according to claim 15, wherein the head component has a shank portion insertable within the hollow bore of the body component, the shank portion of the head component being shorter in length than the hollow bore of the body component such that with the shank portion fully inserted in the body component, at least some hollow space in the hollow bore remains unoccupied by the shank portion.

17. A method according to claim 15, wherein the body component has at least one aperture, the aperture communicating with the hollow bore.

* * * * *